US012618827B2

(12) United States Patent
El Zaatari et al.

(10) Patent No.: US 12,618,827 B2
(45) Date of Patent: May 5, 2026

(54) COMPOSITIONS AND METHODS FOR INDIVIDUALIZED CHARACTERIZATION OF NON-IgE MEDIATED FOOD ALLERGIES

(71) Applicant: The Regents of the University of Michigan, Ann Arbor, MI (US)

(72) Inventors: Mohamad El Zaatari, Ann Arbor, MI (US); John Y. Kao, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 659 days.

(21) Appl. No.: 16/932,227

(22) Filed: Jul. 17, 2020

(65) Prior Publication Data

US 2021/0018490 A1 Jan. 21, 2021

Related U.S. Application Data

(60) Provisional application No. 62/876,399, filed on Jul. 19, 2019.

(51) Int. Cl.
*C12Q 1/68* (2018.01)
*C12Q 1/6883* (2018.01)
*G01N 33/50* (2006.01)

(52) U.S. Cl.
CPC ....... *G01N 33/5023* (2013.01); *C12Q 1/6883* (2013.01); *C12Q 2600/158* (2013.01); *G01N 2800/24* (2013.01)

(58) Field of Classification Search
CPC ........... G01N 33/5023; G01N 2800/24; C12Q 1/6883; C12Q 2600/158
See application file for complete search history.

(56) References Cited

U.S. PATENT DOCUMENTS

| | | | |
|---|---|---|---|
| 4,437,975 A | 3/1984 | Gillespie et al. | |
| 5,538,848 A | 7/1996 | Livak et al. | |
| 5,846,717 A | 12/1998 | Brow et al. | |
| 5,985,557 A | 11/1999 | Prudent et al. | |
| 5,994,069 A | 11/1999 | Hall et al. | |
| 6,001,567 A | 12/1999 | Brow et al. | |
| 6,090,543 A | 7/2000 | Prudent et al. | |
| 6,410,276 B1 | 6/2002 | Burg et al. | |
| 2009/0156540 A1 | 6/2009 | McKenna et al. | |
| 2012/0083007 A1 * | 4/2012 | Nadeau .............. | G01N 33/5094 435/7.24 |

FOREIGN PATENT DOCUMENTS

| | | | | |
|---|---|---|---|---|
| WO | WO90/06995 | 6/1990 | | |
| WO | WO 2004/067726 | 8/2004 | | |
| WO | WO 2005/014861 | * 2/2005 | .............. | C12Q 1/68 |
| WO | WO-2011051402 A1 | * 5/2011 | .......... | C12Q 1/6883 |

OTHER PUBLICATIONS

US 5,962,233 A, 10/1999, Livak et al. (withdrawn)
Gonzalez-Delgado et al., 2016, Pediatric Allergy Immunology, May 27:269-275). (Year: 2016).*
Affymetrix U133 Plus 2.0 (Affymetrix Data Sheet for U133 Plus 2.0 array, 2004). (Year: 2004).*
Rochman et al; J Allergy Clin Immunol. 2017, 140: 738-749.*
International search Report and Written Opinion for PCT/US20/42564. Mailed Dec. 3, 2020. 23 pages.
Bellono et al., Enterochromaffin Cells Are Gut Chemosensors that Couple to Sensory Neural Pathways. Cell. Jun. 29, 2017;170(1):185-198.e16.
Berin, Immunopathophysiology of food protein-induced enterocolitis syndrome. J Allergy Clin Immunol. May 2015;135(5):1108-13.
Burks et al., Prospective oral food challenge study of two soybean protein isolates in patients with possible milk or soy protein enterocolitis. Pediatr Allergy Immunol. Feb. 1994;5(1):40-5.
Chen et al., Induction of Interleukin-9-Producing Mucosal Mast Cells Promotes Susceptibility to IgE-Mediated Experimental Food Allergy. Immunity. Oct. 20, 2015;43(4):788-802.
Chung et al., Expression of transforming growth factor beta1, Transforming growth factor type I and II receptors, and TNF-alpha in the mucosa of the small intestine in infants with food protein-induced enterocolitis syndrome. J Allergy Clin Immunol. Jan. 2002;109(1):150-4.
Gonzalez-Delgado et al., Clinical and immunological characteristics of a pediatric population with food protein-induced enterocolitis syndrome (FPIES) to fish. Pediatr Allergy Immunol. May 2016;27(3):269-75.
Goswami et al., Systemic innate immune activation in food protein-induced enterocolitis syndrome. J Allergy Clin Immunol. Jun. 2017;139(6):1885-1896.e9.
Holbrook et al., Use of ondansetron for food protein-induced enterocolitis syndrome. J Allergy Clin Immunol. Nov. 2013;132(5):1219-20.
Hwang et al., Prospective follow-up oral food challenge in food protein-induced enterocolitis syndrome. Arch Dis Child. Jun. 2009;94(6):425-8.
Hwang, Is This Symptom Even a Food Allergy?: Clinical Types of Food Protein-induced Enterocolitis Syndrome. Pediatr Gastroenterol Hepatol Nutr. Jun. 2014;17(2):74-9.
Jarvinen et al., Intestinal permeability in children with food allergy on specific elimination diets. Pediatr Allergy Immunol. Sep. 2013;24(6):589-95.

(Continued)

*Primary Examiner* — Jehanne S Sitton
(74) *Attorney, Agent, or Firm* — David W. Staple; Casimir Jones, S.C.

(57) ABSTRACT

Provided herein are compositions and methods for the individualized identification of triggers allergies (e.g., non-IgE mediated allergies) in an individual. In particular, biomarkers and assays are provided and used to characterize food allergies and related conditions (e.g., food protein-induced enterocolitis syndrome (FPIES), eosinophilic esophagitis (EoE), etc.) in an individual, by identifying safe and trigger foods without the need for oral challenge.

10 Claims, 4 Drawing Sheets
(4 of 4 Drawing Sheet(s) Filed in Color)

(56) References Cited

OTHER PUBLICATIONS

Jarvinen et al., Food protein-induced enterocolitis syndrome (FPIES): current management strategies and review of the literature. J Allergy Clin Immunol Pract. Jul.-Aug. 2013;1(4):317-22.

Katz et al., Natural history of food protein-induced enterocolitis syndrome. Curr Opin Allergy Clin Immunol. Jun. 2014;14(3):229-39.

Kidd et al., IL1beta- and LPS-induced serotonin secretion is increased in EC cells derived from Crohn's disease. Neurogastroenterol Motil. Apr. 2009;21(4):439-50.

Kimura et al., Cytokine profile after oral food challenge in infants with food protein-induced enterocolitis syndrome. Allergol Int. Jul. 2017;66(3):452-457.

Law, ImmunoAssay: A Practical Guide. Taylor & Francis, Ltd., 2005 edition.

Mcdonald et al., Serum D-xylose absorption tests: reproducibility and diagnostic usefulness in food-induced enterocolitis. J Pediatr Gastroenterol Nutr 1982. 1:533-536.

Miceli Sopo et al., Ondansetron for food protein-induced enterocolitis syndrome. Int Arch Allergy Immunol. 2014;164(2):137-9.

Miceli Sopo et al., , Ondansetron in acute food protein-induced enterocolitis syndrome, a retrospective case-control study. Allergy. Apr. 2017;72(4):545-551.

Motomura et al., Enterochromaffin cell and 5-hydroxytryptamine responses to the same infectious agent differ in Th1 and Th2 dominant environments. Gut. Apr. 2008;57(4):475-81.

Nomura et al., Four distinct subtypes of non-IgE-mediated gastrointestinal food allergies in neonates and infants, distinguished by their initial symptoms. J Allergy Clin Immunol. Mar. 2011;127(3):685-8.e1-8.

Nowak-Wegrzyn et al., Food Protein-Induced Enterocolitis Syndrome. J Investig Allergol Clin Immunol. 2017;27(1):1-18.

Nowak-Wegrzyn et al., Food protein-induced enterocolitis syndrome: Not so rare after all! J Allergy Clin Immunol. Nov. 2017;140(5):1275-1276.

Nowak-Wegrzyn et al., International consensus guidelines for the diagnosis and management of food protein-induced enterocolitis syndrome: Executive summary-Workgroup Report of the Adverse Reactions to Foods Committee, American Academy of Allergy, Asthma & Immunology. J Allergy Clin Immunol. Apr. 2017;139(4):1111-1126.e4.

Obuchowski, Nonparametric analysis of clustered ROC curve data. Biometrics. Jun. 1997;53(2):567-78.

Pena et al., The role of intravenous access during oral food challenges in food protein-induced enterocolitis syndrome. Allergy Asthma Proc. Nov. 1, 2017;38(6):467-473.

Perrier et al., Gut permeability and food allergies. Clin Exp Allergy. Jan. 2011;41(1):20-8.

Price et al., Nuts 'n' guts: transport of food allergens across the intestinal epithelium. Asia Pac Allergy. Oct. 2013;3(4):257-65.

Richard et al., The TNF-family ligand TL1A and its receptor DR3 promote T cell-mediated allergic immunopathology by enhancing differentiation and pathogenicity of IL-9-producing T cells. J Immunol. Apr. 15, 2015;194(8):3567-82.

Rodriguez et al., Intra-class correlation in random-effects models for binary data. The Stata Journal. 2003: 3:32-46.

Ruffner et al., Food protein-induced enterocolitis syndrome: insights from review of a large referral population. J Allergy Clin Immunol Pract. Jul.-Aug. 2013;1(4):343-9.

Samadi et al., The role of gastrointestinal permeability in food allergy. Ann Allergy Asthma Immunol. Aug. 2018;121(2):168-173.

Sampson et al., Food allergy: a practice parameter update—2014. J Allergy Clin Immunol. Nov. 2014;134(5):1016-25.e43.

Sampson, Update on food allergy. J Allergy Clin Immunol. May 2004;113(5):805-19; quiz 820.

Schultz et al., Food protein-induced enterocolitis syndrome from the parent perspective. Curr Opin Allergy Clin Immunol. Jun. 2014;14(3):263-7.

Shimkets, Gene Expression Profiling: Methods and Protocols. 2004, Humana Press.

Sopo et al., A multicentre retrospective study of 66 Italian children with food protein-induced enterocolitis syndrome: different management for different phenotypes. Clin Exp Allergy. Aug. 2012;42(8):1257-65.

Spergel, Nonimmunoglobulin e-mediated immune reactions to foods. Allergy Asthma Clin Immunol. Jun. 15, 2006;2(2):78-85.

Yang et al., Severe Food Protein-Induced Enterocolitis Syndrome to Cow's Milk in Infants. Nutrients. Dec. 22, 2015;8(1):1.

Yu, Intestinal epithelial barrier dysfunction in food hypersensitivity. J Allergy (Cairo). 2012;2012:596081.

European Supplementary Search Report for EP Application No. 20844539.5 dated Jun. 28, 2023 (15 pages).

Dellon, et al., "Markers of eosinophilic inflammation for diagnosis of eosinophilic esophagitis and proton pump inhibitor-responsive esophageal eosinophilia: a prospective study," Clin Gastroenterol Hepatol. 12(12):2015-22 (Dec. 2014).

Kimura, et a., "Serum C-reactive protein in food protein-induced enterocolitis syndrome versus food protein-induced proctocolitis in Japan," Pediatr Int. 58(9):836-41 (Sep. 2016).

Morita, et al., "Antigen-specific T-cell responses in patients with non-IgE-mediated gastrointestinal food allergy are predominantly skewed to T(H)2," J Allergy Clin Immunol. 131(2):590-2.e1-6 (Feb. 2013).

* cited by examiner

COMPOSITIONS AND METHODS FOR INDIVIDUALIZED CHARACTERIZATION OF NON-IgE MEDIATED FOOD ALLERGIES

FIELD

Provided herein are compositions and methods for the individualized identification of triggers allergies (e.g., non-IgE mediated allergies) in an individual. In particular, bio-markers and assays are provided and used to characterize food allergies and related conditions (e.g., a food protein-induced enterocolitis syndrome (FPIES), eosinophilic esophagitis (EoE), etc.) in an individual, by identifying safe and trigger foods without the need for oral challenge.

BACKGROUND

Food protein-induced enterocolitis syndrome (FPIES) is a debilitating disorder in which infants and toddlers react to a wide variety of foods. The disorder usually leads to the child's inability to eat the majority of foods, with the most severe cases allowing for 0-2 tolerated foods only. The reaction to food is severe and comprises profuse vomiting (4-20 times per reaction), with the risk of hypovolemic shock. This reaction is mediated by the immune system, and is delayed, occurring 2-6 hours after trigger food ingestion. Even though FPIES usually resolves on its own at ages 3-5 years, the malnutrition and food aversion that develop during this period often lead to failure to thrive in infants and toddlers and may require a nasogastric feeding tube, or total parenteral nutrition (TPN). Based on the severity of FPIES, there is dire need to develop alternative strategies for the management of this disease.

Eosinophilic esophagitis (EoE) is an allergic swallowing disorder. EoE affects the esophagus, the part of the gastro-intestinal tract (gut) that connects the back of the throat to the stomach. EoE occurs when eosinophils collect in the esophagus, and it is often triggered by food. EoE occurs in both children and adults.

There is no clinical test to identify "safe" versus "trigger" foods for non-IgE mediated allergies (e.g., FPIES, EoE, etc.). For example, for patients with FPIES, typically infants and toddlers, the parents are directed to trial different foods in what is termed oral food challenges (OFCs) to be able to identify safe versus trigger foods. In other words, the parents are directed to randomly trial one food ingredient at a time (repetitively for 5 to 7 days) to identify safe versus trigger foods. In EoE, patients are directed to follow a 4-food elimination diet, and then undergo endoscopy to assess esophageal inflammation. Each of the 4 foods is then re-introduced one a time, and the patients are scoped repeatedly to identify the "safe" versus "trigger" foods. These processes are usually dangerous/painful for the subjects, difficult on parents/patients, and time consuming. Instead of these OFCs and random food challenges, what is needed is a test that accurately identifies "safe" versus "trigger" foods without subjecting the subject to challenges or elimination diets.

SUMMARY

Provided herein are compositions and methods for the individualized identification of safe foods and triggers of non-IgE mediated allergies in an individual. In particular, biomarkers and assays are provided and used to characterize a food protein-induced enterocolitis syndrome (FPIES) in an individual, by identifying safe and trigger foods without the need for oral challenge.

Provided herein are tests that can provide a substitute for food challenges and elimination diets. The tests are performed in culture and circumvents subjugating subjects (e.g., infants and toddlers) to adverse allergic reactions.

In some embodiments, peripheral white blood cells or other cells (e.g., dissociated esophageal biopsy cells) from the patient are treated with various test foods. Gene expression of the cells is then analyzed (e.g., by RT-qPCR) to identify the presence/level of various biomarkers of non-IgE mediated allergies. These biomarkers accurately predict safe (non-trigger) foods.

In some embodiments, provided herein are biomarkers that are indicative of non IgE-mediated allergies (e.g., FPIES, EoE, etc.). In some embodiments, biomarkers are selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, biomarkers are selected from TNFSF15, SPP1, SPINK1, IL-6, CCL3L3, MMP19, CCL20, CCL3, and CXCL2.

In some embodiments, provided herein are methods of assessing the allergic sensitivity of a subject to an item comprising: (a) growing cells from the subject in growth media in contact with the item; (b) detecting the expression level in the cells of one or more biomarkers of allergic sensitivity; (c) comparing the expression level of the one or more biomarkers to threshold and/or control levels of expression; and (d) determining whether the item is a safe substance or trigger substance.

In some embodiments, provided herein are methods of assessing the allergic sensitivity of a subject to an item comprising: (a) growing cells from the subject in growth media in contact with the item; (b) detecting the expression level in the cells of one or more biomarkers of allergic sensitivity; (c) comparing the expression level of the one or more biomarkers to threshold and/or control levels of expression; and (d) determining that the item is a safe substance if the expression level of the one or more bio-markers is beneath the threshold and/or control levels of expression. In some embodiments, if the expression level of the one or more biomarkers is above the threshold and/or control levels of expression, it cannot necessarily be determined that the item is a trigger substance.

In some embodiments, a trigger substance will cause an allergic reaction in the subject if the trigger substance contacts the subject. In some embodiments, a trigger substance will cause non-IgE mediated allergies in the subject if the trigger substance contacts the subject. In some embodiments, a safe substance will not cause an allergic reaction in the subject if the safe substance contacts the subject. In some embodiments, a safe substance will not cause non-IgE mediated allergies in the subject if the safe substance contacts the subject. In some embodiments, the item is a food item. In some embodiments, a trigger food item will induce and/or exacerbate protein-induced entero-colitis syndrome (FPIES) in the subject if ingested. In some embodiments, a trigger food item will induce and/or exacerbate eosinophilic esophagitis (EoE) in the subject if ingested. In some embodiments, the subject exhibits symptoms of allergic sensitivities to one or more unknown items. In some embodiments, the subject suffers from non-IgE mediated allergic reactions to one or more unknown items. In some embodiments, the subject suffers from FPIES. In some embodiments, the subject suffers from EoE.

In some embodiments, growing cells in growth media comprises cell culture in liquid media. In some embodiments, the cells are white blood cells or other cells (e.g., dissociated esophageal biopsy cells). In some embodiments, the item is added to the growth media as a liquid or homogenized sample.

In some embodiments, the expression level comprises the RNA expression level. In some embodiments, the level of one or more mRNA biomarkers of allergic sensitivity in the cells is quantified. In some embodiments, the level of one or more mRNA biomarkers of allergic sensitivity is quantified by any suitable methods, such as, nuclease protection assay, Northern blotting, RT-qPCR, or other suitable methods described herein and/or understood in the field.

In some embodiments, the expression level comprises the protein expression level. In some embodiments, the level of one or more protein biomarkers of allergic sensitivity in the cells is quantified. In some embodiments, the level of one or more protein biomarkers of allergic sensitivity is quantified by any suitable methods, such as, enzyme-linked immunosorbent assay (ELISA) mass spectrometry, or other suitable methods described herein and/or understood in the field.

In some embodiments, the one or more biomarkers (e.g., 1, 2, 3, 4, 5, 6, 7, 8, 9 10, 11, 12, 13, 14, 15, 16, 17, 18, 19, 20, 21, 22, 23, 24, 26, or ranges therebetween) are selected from: TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, expression of a panel of biomarkers is quantified, and wherein the panel comprises 1000 or fewer biomarkers (e.g., 100 biomarkers, 800 biomarkers, 600 biomarkers, 400 biomarkers, 200 biomarkers, 100 biomarkers, 50 biomarkers, 30 biomarkers, or ranges therebetween). In some embodiments, the panel comprises three or more biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, the panel comprises six or more biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, the panel comprises five or more biomarkers selected from TNFSF15, SPP1, SPINK1, IL-6, CCL3L3, MMP19, CCL20, CCL3, and CXCL2. In some embodiments, the panel comprises TNFSF15, SPP1, SPINK1, IL-6, CCL3L3, MMP19, CCL20, CCL3, and CXCL2.

In some embodiments, a threshold level of expression is based on population expression levels. In some embodiments, a control level of expression is based on expression levels in the subject in response to a known trigger substance and/or known safe substance.

In some embodiments, provided herein are methods of assessing the allergic sensitivity of a subject to a food comprising: (a) growing white blood cells from the subject in cell culture media in contact with the food item; (b) detecting the expression level in the white blood cells of a panel of biomarkers of allergic sensitivity comprising biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF; (c) comparing the expression level of the panel of biomarkers to threshold and/or control levels of expression for the panel of biomarkers; and (d) determining whether the item is a safe food or trigger food. In some embodiments, provided herein are methods of assessing the allergic sensitivity of a subject to a food comprising: (a) growing white blood cells from the subject in cell culture media in contact with the food item; (b) detecting the expression level in the white blood cells of a panel of biomarkers of allergic sensitivity comprising biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF; (c) comparing the expression level of the panel of biomarkers to threshold and/or control levels of expression for the panel of biomarkers; and (d) determining that the item is a safe substance if the expression level of the one or more biomarkers is beneath the threshold and/or control levels of expression. In some embodiments, if the expression level of the one or more biomarkers is above the threshold and/or control levels of expression, it cannot necessarily be determined that the item is a trigger substance. In some embodiments, methods further comprise obtaining a biological sample from the subject. In some embodiments, the biological sample is a blood sample. In some embodiments, the food item is a liquid food item. In some embodiments, the food item is homogenized into a liquid sample comprising particulates of the food item. In some embodiments, a trigger substance will cause a non-IgE mediated allergic reaction if the trigger food is ingested by the subject. In some embodiments, a safe substance will not cause a non-IgE mediated allergic reaction if the safe food is ingested by the subject. In some embodiments, a trigger food item will induce and/or exacerbate protein-induced enterocolitis syndrome (FPIES) in the subject if ingested. In some embodiments, the subject exhibits symptoms of allergic sensitivities to one or more unknown items. In some embodiments, the subject suffers from non-IgE mediated allergic reactions to one or more unknown items. In some embodiments, the subject suffers from FPIES. In some embodiments, the level of one or more mRNA biomarkers of allergic sensitivity in the cells is quantified. In some embodiments, the level of one or more mRNA biomarkers of allergic sensitivity is quantified by nuclease protection assay, Northern blotting, RT-qPCR, or other suitable methods described herein and/or understood in the field. In some embodiments, the panel comprises 1000 or fewer biomarkers (e.g., 100 biomarkers, 800 biomarkers, 600 biomarkers, 400 biomarkers, 200 biomarkers, 100 biomarkers, 50 biomarkers, 30 biomarkers, or ranges therebetween). In some embodiments, the panel comprises three or more biomarkers (e.g., 3, 4, 5, 6, 7, 8, 9, 10, 11, 12, 13, 14, 15, 16, 17, 18, 19, 20, 21, 22, 23, 24, 26, or ranges therebetween) selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, the panel comprises three or more biomarkers (e.g., 3, 4, 5, 6, 7, 8, 9, or ranges therebetween) selected from TNFSF15, SPP1, SPINK1, IL-6, CCL3L3, MMP19, CCL20, CCL3, and CXCL2. In some embodiments, the panel comprises TNFSF15, SPP1, SPINK1, IL-6, CCL3L3, MMP19, CCL20, CCL3, and CXCL2. In some embodiments, a threshold level of expression is based on population expression levels. In some embodiments, a control level of expression is based on expression levels in the subject in response to a known trigger substance and/or known safe substance.

In some embodiments, provided herein are methods of assessing the allergic sensitivity of a subject to a food comprising: (a) growing dissociated esophageal biopsy cells from the subject in cell culture media in contact with the food item; (b) detecting the expression level in the dissociated esophageal biopsy cells of a panel of biomarkers of allergic sensitivity comprising biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF; (c) comparing the expression level of the panel of biomarkers to threshold and/or control levels of expression for the panel of biomarkers; and (d) determining whether the item is a safe food or trigger food.

In some embodiments, provided herein are methods of assessing the allergic sensitivity of a subject to a food comprising: (a) growing dissociated esophageal cells from mucosal biopsies from the subject in cell culture media in contact with the food item; (b) detecting the expression level in the cells of a panel of biomarkers of allergic sensitivity comprising biomarkers selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF; (c) comparing the expression level of the panel of biomarkers to threshold and/or control levels of expression for the panel of biomarkers; and (d) determining that the item is a safe substance if the expression level of the one or more biomarkers is beneath the threshold and/or control levels of expression. In some embodiments, if the expression level of the one or more biomarkers is above the threshold and/or control levels of expression, it cannot necessarily be determined that the item is a trigger substance. In some embodiments, methods further comprise obtaining a biological sample from the subject. In some embodiments, the biological sample is a mucosal biopsy. In some embodiments, the food item is a liquid food item. In some embodiments, the food item is homogenized into a liquid sample comprising particulates of the food item. In some embodiments, a trigger substance will cause a non-IgE mediated allergic reaction if the trigger food is ingested by the subject. In some embodiments, a safe substance will not cause a non-IgE mediated allergic reaction if the safe food is ingested by the subject. In some embodiments, a trigger food item will induce and/or exacerbate eosinophilic esophagitis (EoE) in the subject if ingested. In some embodiments, the subject exhibits symptoms of allergic sensitivities to one or more unknown items. In some embodiments, the subject suffers from non-IgE mediated allergic reactions to one or more unknown items. In some embodiments, the subject suffers from eosinophilic esophagitis (EoE). In some embodiments, the level of one or more mRNA biomarkers of allergic sensitivity in the cells is quantified. In some embodiments, the level of one or more mRNA biomarkers of allergic sensitivity is quantified by nuclease protection assay, Northern blotting, RT-qPCR, or other suitable methods described herein and/or understood in the field. In some embodiments, the panel comprises 1000 or fewer biomarkers (e.g., 100 biomarkers, 800 biomarkers, 600 biomarkers, 400 biomarkers, 200 biomarkers, 100 biomarkers, 50 biomarkers, 30 biomarkers, or ranges therebetween). In some embodiments, the panel comprises three or more biomarkers (e.g., 3, 4, 5, 6, 7, 8, 9, 10, 11, 12, 13, 14, 15, 16, 17, 18, 19, 20, 21, 22, 23, 24, 26, or ranges therebetween) selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, the panel comprises three or more biomarkers (e.g., 3, 4, 5, 6, 7, 8, 9, or ranges therebetween) selected from TNFSF15, SPP1, SPINK1, IL-6, CCL3L3, MMP19, CCL20, CCL3, and CXCL2. In some embodiments, the panel comprises TNFSF15, SPP1, SPINK1, IL-6, CCL3L3, MMP19, CCL20, CCL3, and CXCL2. In some embodiments, a threshold level of expression is based on population expression levels. In some embodiments, a control level of expression is based on expression levels in the subject in response to a known trigger substance and/or known safe substance.

In some embodiments, provided herein are panels of biomarkers comprising three or more cDNAs selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, one or more of the cDNAs span an exon/exon junction. In some embodiments, all of the cDNAs span exon/exon junctions. In some embodiments, one or more of the cDNAs are full-length cDNAs. In some embodiments, all of the cDNAs are full-length cDNAs. In some embodiments, the panel comprises 1000 or fewer biomarkers (e.g., 100 biomarkers, 800 biomarkers, 600 biomarkers, 400 biomarkers, 200 biomarkers, 100 biomarkers, 50 biomarkers, 30 biomarkers, or ranges therebetween). In some embodiments, the panel comprises three or more biomarkers (e.g., 3, 4, 5, 6, 7, 8, 9, 10, 11, 12, 13, 14, 15, 16, 17, 18, 19, 20, 21, 22, 23, 24, 26, or ranges therebetween) selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, the panel comprises three or more biomarkers (e.g., 3, 4, 5, 6, 7, 8, 9, or ranges therebetween) selected from TNFSF15, SPP1, SPINK1, IL-6, CCL3L3, MMP19, CCL20, CCL3, and CXCL2. In some embodiments, the panel comprises TNFSF15, SPP1, SPINK1, IL-6, CCL3L3, MMP19, CCL20, CCL3, and CXCL2.

BRIEF DESCRIPTION OF THE DRAWINGS

The patent or application file contains at least one drawing executed in color. Copies of this patent or patent application publication with color drawings will be provided by the Office upon request and payment of the necessary fee.

DEFINITIONS

Figure 1:
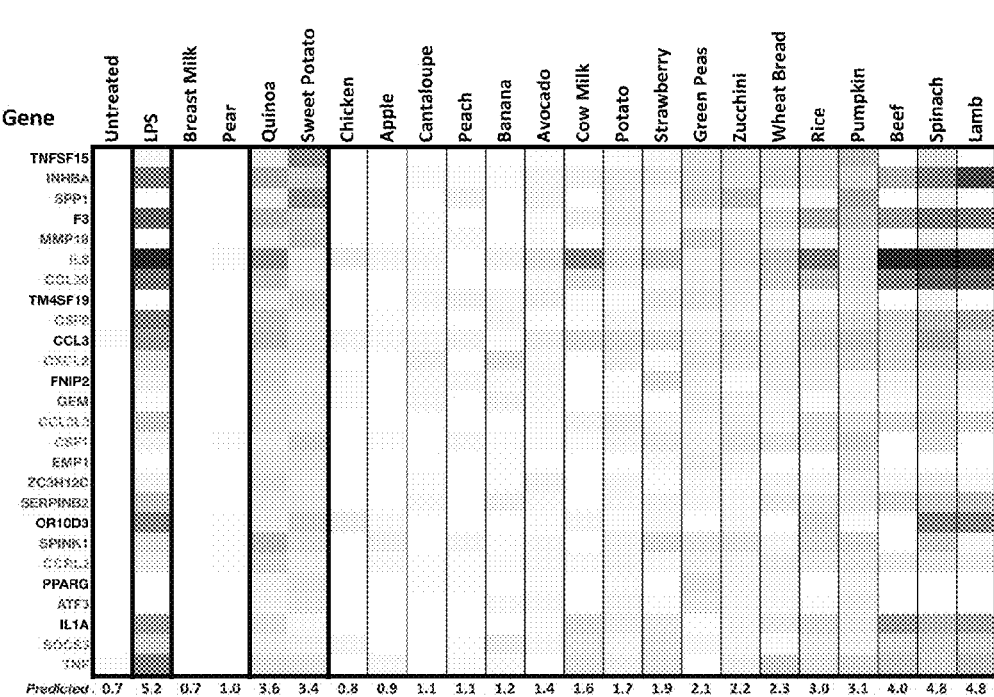
FIG. 1. Full microarray heatmap of 26-gene panel of the transcriptional gene panel associated with FPIES. Each row represents one gene while each column represents a different food treatment. The color range (blue-white-red-purple) indicates how high the gene expression is for a particular gene under in response to the assigned treatment.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a CPS1 peptide" is a reference to one or more CPS1 peptides and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C."

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including human and non-human animals (e.g., dogs, cats, cows, horses, sheep, poultry, fish, crustaceans, etc.). As used herein, the term "patient" typically refers to a subject that is being treated for a disease or condition.

As used herein, the term "preventing" refers to prophylactic steps taken to reduce the likelihood of a subject (e.g., an at-risk subject, a subject suffering from acute internal tissue injury) from contracting or suffering from a particular disease, disorder or condition. The likelihood of the disease, disorder or condition occurring in the subject need not be reduced to zero for the preventing to occur; rather, if the steps reduce the risk of a disease, disorder or condition across a population, then the steps prevent the disease, disorder or condition within the scope and meaning herein.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), mucosal biopsy tissue, sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate (e.g., bronchoalveolar lavage), bronchial brushing, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, pancreas, and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

As used herein, the term "trigger substance" refers to anything that elicits an allergic response (e.g., non-IgE mediated allergic reaction) in an individual. A "trigger food" is a food item that elicits an allergic response (e.g., non-IgE mediated allergic reaction) in an individual.

As used herein, the term "safe substance" refers to anything that does not elicit an allergic response (e.g., non-IgE mediated allergic reaction) in an individual. A "trigger food" is a food item that does not elicit an allergic response (e.g., non-IgE mediated allergic reaction) in an individual.

DETAILED DESCRIPTION

Provided herein are compositions and methods for the individualized identification of triggers of non-IgE mediated allergies in an individual. In particular, biomarkers and assays are provided and used to characterize a food protein-induced enterocolitis syndrome (FPIES) in an individual, by identifying safe and trigger foods without the need for oral challenge.

Experiments conducted during development of embodiments herein have identified a set of biomarkers that exhibit altered (e.g., elevated or decreased) levels of expression (e.g., protein expression, mRNA expression, etc.) in a subject's cells (e.g., white blood cells) when the cells have been exposed to an allergen (e.g., food allergen) that the subject is sensitive to (e.g., allergic to (e.g., via non-IgE mediated allergies)). In some embodiments, the biomarkers herein allow direct assaying of cellular response to potential allergens via culturing of cells in the presence of potential allergens and measuring the expression levels of all or a subset (e.g., a panel) of the biomarkers herein.

Embodiments herein comprise obtaining a biological sample (e.g., comprising cells (e.g., comprising white blood cells (WBCs), dissociated esophageal biopsy cells, etc.)) from a subject. In some embodiments, cells (e.g., WBCs) are isolated from the sample and placed in growth media (e.g., plated into tissue culture well plates). In some embodiments, the cells (e.g., WBCs) are allowed to grow (culture) in/on the media. In some embodiments, potential allergens (e.g., foods, food ingredients, whole foods, etc.) are added to the cells (e.g., WBCs). In some embodiments, a single potential allergen is added to each well. In some embodiments, the cells are allowed to grow (culture) in the presence of the potential allergen. In some embodiments, gene expression of various selected biomarkers is characterized by any suitable method for detection of gene expression and/or level of production of gene product (e.g., by RT-qPCR, by microarray, antibody detection, etc.) for the allergen-treated cells. In some embodiments, the biomarker gene expression of the potential-allergen-treated cells are compared to control cells (e.g., untreated cells, liposaccharide (LPS) treatment, etc.). In some embodiments, the biomarker gene expression of the potential-allergen-treated are compared to control cells (e.g., untreated cells, liposaccharide (LPS) treatment, etc.). In some embodiments, the biomarker gene expression of the potential-allergen-treated are compared to biomarker gene expression of known safe and trigger substances (e.g., foods). In some embodiments, comparison of the biomarker gene expression profiles of the potential-allergen-treated cells with control profiles and/or profiles of known safe and trigger substances (e.g., for the individual) provides an individualized characterization of the safe and trigger substances (e.g., foods) for the individual.

In some embodiments, the present invention provides biomarkers (e.g., selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF), the level of expression of which in immune cells, or dissociated esophageal biopsy cells, is predictive whether a substance that the cells have been exposed to is a trigger for allergic reaction (non-IgE mediated allergy). In some embodiments, gene expression levels and/or concentration (e.g., of mRNA, of protein) in immune cells (e.g., WBCs) or dissociated esophageal biopsy cells, obtained from a test sample (e.g., blood, mucosal biopsy, etc.) of biomarkers are significantly altered when the cultured cells are grown in the presence of a trigger substance (e.g., compared to a safe substance, compared to control, etc.).

In a particular embodiment, blood (or other cell-containing (e.g., WBC-containing) biological sample) is obtained from a subject and WBCs are isolated (e.g., by lysing the red blood cells, and washing and/or capturing the WBCs). The WBCs are plated into tissue culture well plates, and different food homogenates (e.g., potential allergens) are added to the cells of each well. In some embodiments, the panel of foods is determined based on nutritional deficiencies of the patient (e.g., selected from a large standardized food panel). In some embodiments, foods are selected from a known panel of potential safe and trigger foods. In some embodiments, likely safe foods and possible alleges are included. In some embodiments, the subject's known safe foods versus trigger foods are included (e.g., as controls). In some embodiments, known safe/trigger foods have previously been determined by oral challenge of 'real-world' experience. In some embodiments, at least one (e.g., at least two (e.g., 2, 4, 5, or more)) known safe foods and one (e.g., at least two (e.g., 2, 4, 5, or more)) known trigger foods are used as controls. In some embodiments, untreated and LPS treatment are also used as baseline negative and positive controls. In some embodiments, the cells are cultured in the presence of the food homogenates for a period of time (e.g., 10 minutes, 20 minutes, 30 minutes, 45 minutes, 1 hour, 2 hours, 3 hours, 4 hours, 6 hours, 8 hours, 12 hours, 24 hours, or more, or ranges therebetween). In some embodiments, gene expression profiles are obtained of the test and control cells. Gene expression (e.g., protein expression, mRNA expression, etc.) may be quantified by any suitable methods or technologies. In some embodiments, RNA is extracted and the expression pattern of the identified gene panel is measured for each food treatment. In some embodiments, RT-qPCR is used to quantify the gene expression of each of a panel of biomarkers. In some embodiments, the biomarker gene expression of the potential-allergen-treated cells are compared to control cells (e.g., untreated cells, liposaccharide (LPS) treatment, etc.). In some embodiments, the biomarker gene expression of the potential-allergen-treated are compared to control cells (e.g., untreated cells, liposaccharide (LPS) treatment, etc.). In some embodiments, the biomarker gene expression of the potential-allergen-treated are compared to biomarker gene expression of known safe and trigger substances (e.g., foods). In some embodiments, comparison of the biomarker gene expression profiles of the potential-allergen-treated cells with control profiles and/or profiles of known safe and trigger substances (e.g., for the individual) provides an individualized characterization of the safe and trigger substances (e.g., foods) for the individual.

In other embodiments, similar steps to those above are performed using a dissociated esophageal biopsy sample instead of blood.

In some embodiments, the biomarkers assessed are selected from TNFSF15, INHBA, SPP1, F3, MMP19, IL6, CCL20, TM4SF19, CSF2, CCL3, CXCL2, FNIP2, GEM, CCL3L3, CSF1, EMP1, ZC3H12C, SERPINB2, OR10D3, SPINK1, CCRL2, PPARG, ATF3, IL1A, SOCS3, and TNF. In some embodiments, gene expression for two or more (e.g., 2, 3, 4, 5, 6, 7, 8, 9, 10, 11, 12, 13, 14, 15, 16, 17, 18, 19, 20, 21, 22, 23, 24, 25, 26, or ranges therebetween) of the above biomarkers is assessed (e.g., comparing expression after exposure to a potential allergen to control expression). In some embodiments, gene expression for two or more (e.g., 2, 5, 10, 20, 50, 100, 200, 500, 750, 1000, or more or ranges therebetween) total biomarkers (e.g., not limited to the above biomarkers) is assessed.

In some embodiments, the biomarkers assessed are selected from TNFSF15, SPP1, SPINK1, IL-6, CCL3L3, MMP19, CCL20, CCL3, and CXCL2. In some embodiments, gene expression for two or more (e.g., 2, 3, 4, 5, 6, 7, 8, 9, or ranges therebetween) of the above biomarkers is assessed (e.g., comparing expression after exposure to a potential allergen to control expression). In some embodiments, gene expression for two or more (e.g., 2, 5, 10, 20, 50, 100, 200, 500, 750, 1000, or more or ranges therebetween) total biomarkers (e.g., not limited to the above biomarkers) is assessed.

Allergies occur when a subject's immune system reacts to a foreign substance, such as pollen, bee venom, pet dander, or a food. Typically, these foreign substances do not elicit an immune response in the general population. In a common allergic reaction, the immune system overreacts to the presence of an allergen by producing Immunoglobulin E (IgE) antibodies. These antibodies travel to cells that release chemicals, causing an allergic reaction. This reaction usually causes symptoms in the nose, lungs, throat, or on the skin. Reproducible adverse reactions which occur after eating a food but that are not mediated by immunologic mechanisms are classified as food intolerances and can occur by metabolic, pharmacologic, toxic or undefined mechanisms. Classic examples of food intolerance include lactose intolerance and scombroid fish poisoning. In contrast, a food allergy is a reproducible, adverse health event occurring after exposure to a specific food that is mediated by an immunologic mechanism. Food allergy reactions can be mediated by IgE- or non-IgE mediated mechanisms. Both mechanisms of allergy require an immunologic sensitization to the food antigen which results in a reproducible, immune-mediated reaction upon re-exposure to the food.

Food protein-induced enterocolitis syndrome (FPIES) is a non-IgE mediated allergy. FPIES can be divided into two forms: acute and chronic. The acute form is the more common form and is characterized by profuse repetitive emesis and lethargy that begins 1-4 hours following ingestion of the causal food (Sampson et al. 2014. J Allergy Clin Immunol. 2014; 134(5):1016-1025; incorporated by reference in its entirety). It is often accompanied by decreased activity, lethargy, pallor, diarrhea, and in 15% of cases may proceed to severe systemic symptoms which include hypothermia, methemoglobinemia, acidemia, and hypotension. These acute reactions are often accompanied by leukocytosis with neutrophilia and thrombocytosis, though these laboratory findings are not specific for FPIES. Alternatively, if a causal food is being ingested every day, children may develop chronic FPIES. Chronic FPIES is less common and has been difficult to diagnose with certainty. It typically occurs in children who have been ingesting the offending food on a daily basis and presents with chronic/intermittent emesis or reflux, watery diarrhea, and may progress to weight loss or failure to thrive. The diagnosis of FPIES is certain if the symptoms improve with withdrawal of offending food and acute symptoms of FPIES are present when it is reintroduced (e.g., vomiting 1-4 hours following food challenge). Due to the nonspecific symptoms and lack of provider familiarity with the diagnosis, many patients with FPIES experience delay to diagnosis or misdiagnosis (Schultz & Westcott-Chavez Curr Opin Allergy Clin Immunol. 2014; 14(3):263-267; Katz & Goldberg. Curr Opin Allergy Clin Immunol. 2014; 14(3):229-239.; incorporated by reference in their entireties).

The most common FPIES triggers in a geographic region may reflect the pattern of infant food introduction in that area. For example, in the US, FPIES often presents in infancy with reaction to cow's milk and soy under 6 months of age, or slightly older children with reactions to grains like rice, wheat or oat. Reactions to grains such as rice, oat or wheat are the next most common group, but reactions to egg, meats, vegetables and fruits have also been described.

Primary eosinophilic gastrointestinal disorders (EGID) are characterized by eosinophilic infiltrate into the gastrointestinal tissue in the absence of another demonstrable cause and include: eosinophilic esophagitis (EoE), eosinophilic gastritis, gastroenteritis, enteritis, and colitis. Eosinophilic esophagitis (EoE) is the most common of the eosinophilic gastrointestinal disorders. It is estimated to have a prevalence of approximately 1/2000, which may be rising, and is most common in Caucasian males. In children, EoE is more likely to present with abdominal pain, nausea, emesis and failure to thrive. In adolescents and adult, symptoms of heartburn, dysphagia, food impaction and stricture are more common. The diagnostic gold standard for EoE is the presence of at least 15 eos/high power field (hpf) in esophageal biopsy taken from multiple sites obtained with esophagogastroduodenoscopy (EGD) after recommended 8 weeks of maximum proton pump inhibitor (PPI) dose. While most EGID are unknown to clearly have a food-related pathogenesis, EoE, can be managed by dietary avoidance, topical corticosteroids and, if needed, interventions such as esophageal dilatation.

Some embodiments herein comprise obtaining a biological sample from a subject for analysis. In some embodiments, the subject suffers from, or is suspected to suffer from a non-IgE mediated allergic condition (e.g., FPIES, EoE, etc.). In some embodiments, the subject has undergone dietary challenge and/or an elimination diet in order to identify trigger/safe foods. In some embodiments, the analysis described herein is performed prior to or in place of dietary challenge and/or an elimination diet.

In some embodiments, a biological sample comprises immune cells. In some embodiments, a sample comprises white blood cells. In some embodiments, a sample comprises one or more of neutrophils, lymphocytes, eosinophils, monocytes, and basophils. In some embodiments, a biological sample is a blood sample (e.g., whole blood, processed blood, plasma, etc.). In some embodiments, a biological sample has been processed to dissociate total cells from one or more other components of the unprocessed sample. In some embodiments, a sample comprises white blood cells separated from other blood components (e.g., red blood cells). In some embodiments, a biological sample is a mucosal biopsy (e.g., from the esophagus). In some embodiments, a biological sample comprises dissociated esophageal biopsy cells. In some embodiments, a biological sample comprises total esophageal cells isolated from one or more other components of mucosal biopsy (e.g., epithelial cells, immune cells etc.).

In some embodiments, immune cells (e.g., WBCs) or dissociated esophageal biopsy cells are grown in/on appropriate media for the cell type. In some embodiments, media is liquid media. In some embodiments, media is solid media, In some embodiments, cells are cultured in the presence of a test substance (e.g., test food). In some embodiments, the sample (e.g., comprising immune cells, or dissociated esophageal biopsy cells) is divided into multiple (e.g., 4, 6, 8, 10, 12, 18, 24, 36, 48, 60, 72, 84, 96, 192, 384, or more or ranges therebetween) test samples. In some embodiments, each test sample is exposed to a test substance (e.g., test food). In some embodiments, each test sample is exposed to a different test substance (e.g., test food). In some embodiments, replicates of each test substance (e.g., test food) are performed. In some embodiments, the cells are cultured in the presence of the test substance (e.g., test food) for a period of time (e.g., 10 minutes, 20 minutes, 30 minutes, 45 minutes, 1 hour, 2 hours, 3 hours, 4 hours, 6 hours, 8 hours, 12 hours, 24 hours or more, or ranges therebetween). In some embodiments, the cells are cultured in the absence of the test substance (e.g., test food) for a period of time prior to addition of the food substance. In some embodiments, a control sample is cultured without addition of a test substance (e.g., test food), in the presence of a control substance, or in the presence of a known safe substance (e.g., safe food).

Following culture of the cells in the presence of the test substance (e.g., test food), the expression (e.g., protein expression, mRNA expression) of the cells is analyzed. In some embodiments, the expression of various biomarkers described herein is analyzed.

Some exemplary methods described herein utilize RT-qPCR to quantitate mRNA expression of biomarker genes; however, embodiments herein are not so limited. In some embodiments, any technique/method that measures gene or protein expression of the biomarkers herein may find use in embodiments herein.

There are various known techniques by which biomarker levels may be measured. Thus, by biomarker levels is meant the level of expression and/or activity and/or amount and/or concentration of the biomarker. Expression levels may be measured at the level of protein or mRNA according to any suitable method.

The expression level and/or amount and/or concentration of a biomarker (e.g. mRNA, protein, etc.) may rely upon a binding reagent such as an antibody, aptamer, nucleic acid probe, or other binding agent that binds specifically to the biomarker of interest e.g. mRNA, protein, etc.). The antibody may be of monoclonal or polyclonal origin. Fragments and derivative antibodies may also be utilized, to include without limitation Fab fragments, ScFv, single domain antibodies, nanoantibodies, heavy chain antibodies, aptamers etc. which retain specific binding function and these are included in the definition of "antibody." Such antibodies are useful in certain embodiments of the invention.

In certain embodiments the expression level and/or amount and/or concentration of a marker is determined using an antibody, aptamer, nucleic acid probe, or other binding agent conjugated to a label. By label is meant a component that permits detection, directly or indirectly. For example, the label may be an enzyme, optionally a peroxidase, a fluorophore, etc.

Additional techniques for determining expression level at the level of protein and/or the amount and/or concentration of a marker include, for example, Western blot, immunoprecipitation, immunocytochemistry, mass spectrometry, ELISA and others (see ImmunoAssay: A Practical Guide, edited by Brian Law, published by Taylor & Francis, Ltd., 2005 edition; incorporated by reference in its entirety). Levels of protein may be detected using a lateral flow assay or solid phase detection assay, in some embodiments.

In some embodiments, the levels of mRNA biomarkers are measured in a biological sample. Accordingly, in specific embodiments the expression level is determined by microarray, northern blotting, sequencing, nucleic acid amplification, etc. Nucleic acid amplification includes PCR and all variants thereof such as real-time and end-point methods, RT-PCR, qPCR, RT-qPCR, etc. Other nucleic acid amplification techniques are well known in the art, and include methods such as NASBA, 3SR and Transcription Mediated Amplification (TMA). Other suitable amplification methods include the ligase chain reaction (LCR), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO 90/06995), invader technology, strand displacement technology, recombinase polymerase amplification (RPA), nicking enzyme amplification reaction (NEAR) and nick displacement amplification (WO 2004/067726). This list is not intended to be exhaustive; any nucleic acid amplification technique may be used provided the appropriate nucleic acid product is specifically amplified. Design of suitable primers and/or probes is within the capability of one skilled in the art. Various primer design tools are freely available to assist in this process such as the NCBI Primer-BLAST tool. Primers and/or probes may be at least 15, 16, 17, 18, 19, 20, 21, 22, 23, 24 or 25 (or more) nucleotides in length. mRNA expression levels may be measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

RNA expression may be determined by hybridization of RNA to a set of probes. The probes may be arranged in an array. Microarray platforms include those manufactured by companies such as Affymetrix, Illumina and Agilent. RNA expression may also be measured using next generation sequencing methods, such as RNA-seq. This may require conversion of RNA to cDNA or may be a direct RNA sequencing methodology. In embodiments in which a biomarker is a protein (and protein expression levels are measured), polypeptide and/or peptide, detection and/or quantification reagents may comprise antibodies or antibody-like reagents, aptamers, etc. that bind (e.g., specifically) to the biomarker(s). In such embodiments, detection and/or quantification may be achieved by, for example, an immunoassay, Western blot, enzyme-linked immunosorbent assay (ELISA), radioimmunoassay (RIA), fluorometric assay, or other suitable assays known in the field.

In embodiments in which a biomarker is an RNA (e.g., mRNA), and RNA expression levels are measured, detection and/or quantification reagents may comprise primers (e.g., for amplification, reverse transcription, etc.) or probes (e.g., detectably-labeled (e.g., optically-labeled, fluorescently labeled, etc.) oligonucleotides) that bind (e.g., specifically) to the biomarker. In such embodiments, detection and/or quantification may be achieved by, for example, RT-PCR, qPCR, RT-qPCR, Northern blot analysis, an enzymatic cleavage assay (e.g., INVADER, Hologic, Inc.; See e.g., U.S. Pat. Nos. 5,846,717, 6,090,543; 6,001,567; 5,985,557; and 5,994,069; each of which is herein incorporated by reference), a hybridization assay (e.g., TaqMan assay (Life Technologies; See e.g., U.S. Pat. Nos. 5,962,233 and 5,538, 848, each of which is herein incorporated by reference), etc.

Levels of mRNA may be detected using a lateral flow assay or solid phase detection assay, in some embodiments.

In some embodiments, assays are performed using point-of-care devices and systems such as lateral flow devices, paper-based spot tests, dip stick tests, lab-on-a-chip, microfluidic devices, pre-filled 96-well microtiter plates, and the like.

In some embodiments, gene expression of a panel of genes is compared to a threshold or control by calculating a score (e.g., risk score) for a test item (e.g., food). The risk score of the test item is then compared to a threshold risk score, and if the item's risk score is less than a control or threshold risk score, then the item is deemed safe. In some embodiments, assessing a test item comprises: (i) calculating a risk score based on the expression of biomarkers; and (ii) comparing the risk score to a threshold to determine the item is a safe item. In some embodiments, the genes in a panel are weighted to calculate a risk score. In some embodiments, genes that are more highly correlated with trigger are weighted more heavily in calculating a risk score. In some embodiments, the levels of all genes in a panel are equally weighted.

Experimental

EXAMPLE 1

Experiments were conducted during development of embodiments herein to demonstrate the capacity of the biomarkers herein to differentiate safe and trigger foods. The protocol of an exemplary demonstration is described below. The following exemplifies an embodiment of the present invention but does not limit the scope of embodiments herein.

Figure 2A:
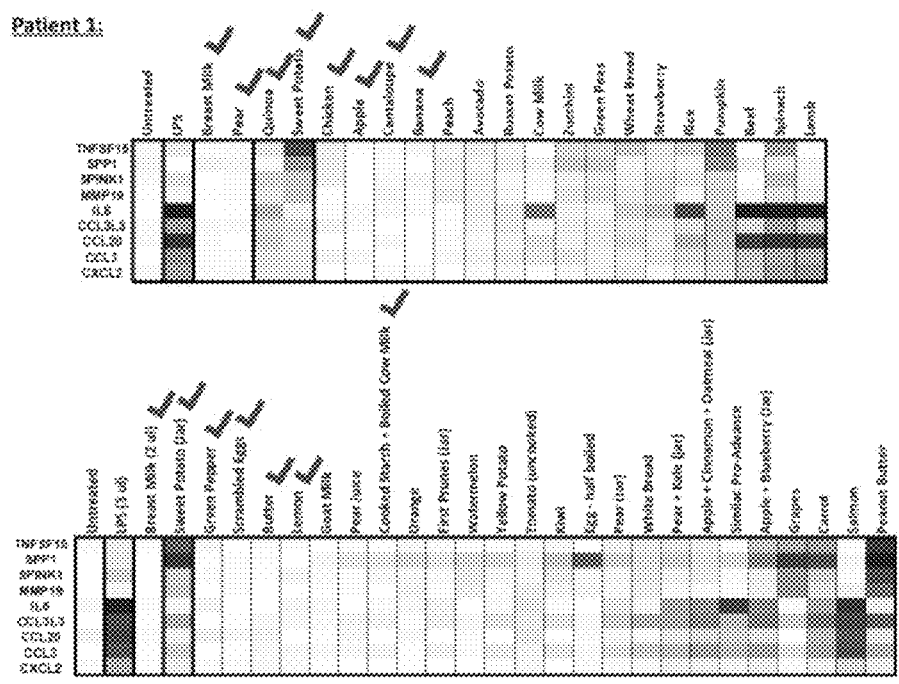
FIG. 2A-B. RT-qPCR heatmap panel of the 9-gene transcriptional gene panel associated with FPIES for Each row represents one gene while each column represents a different food treatment. The color range (blue-white-red-purple) indicates how high the gene expression is for a particular gene under in response to the assigned treatment. (A) Patient 1; (B) Patient 2. Green check marks represent correct predictions of safe and trigger foods; red X's represent incorrect predictions (false positives) of trigger foods that were actually safe; no trigger foods were incorrectly predicted to be safe (no false negatives).
Figure 2A:
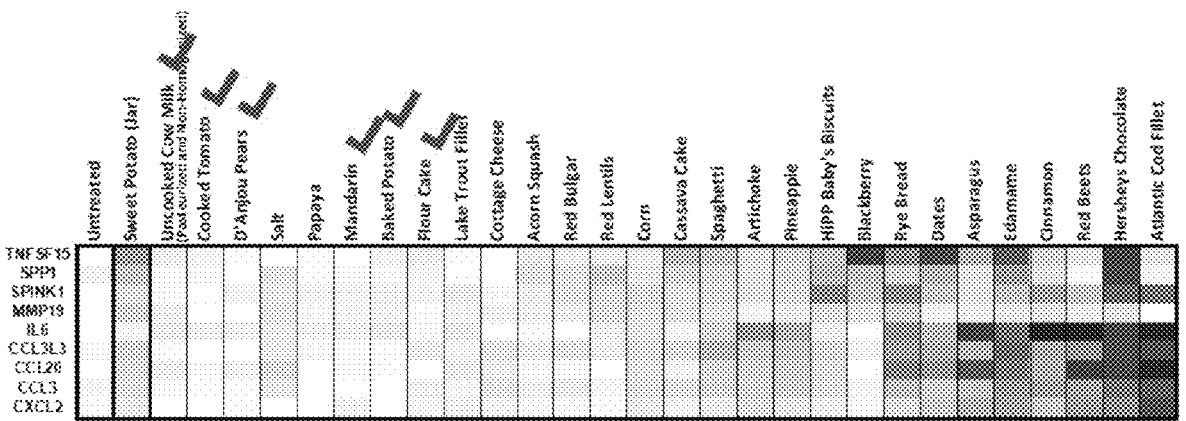
Figure 2B:
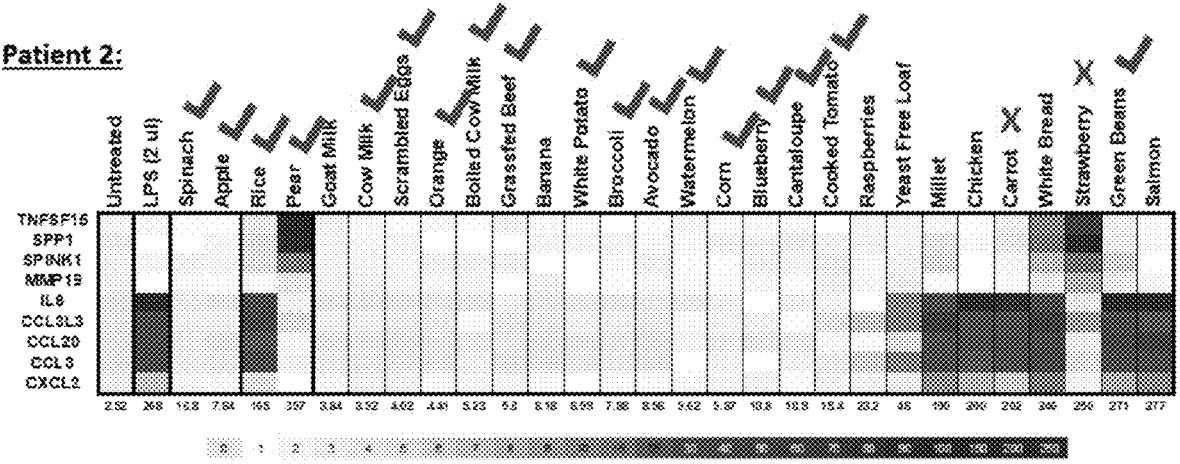

6 ml of blood was withdrawn from a patient into lavender top K2EDTA tubes. 20 ml of ACK buffer was added to the blood and incubated at 4° C. for 10 min to lyse the red blood cells. The solution was topped up to 50 ml with $Ca^{2+}$- and $Mg^{2+}$-free PBS. The solution centrifuged at 450×g. The supernatant was decanted. The WBC pellet was resuspended and washed again in 20 ml ACK at 4° C. for 10 min. The PBS wash and centrifugation steps were repeated. 5 ml of ACK was added to the pellet and incubated for 5 minutes at 4° C. The PBS wash and centrifugation steps were again repeated. The WBC pellet was resuspended in 16 ml of RPMI plus 10% FBS. The cell suspension was divided into 500 μl aliquots in 24-well cell culture plates. Undigested solid test foods were added to a separate wells of a culture plate, suspended in 2×volume RPMI+10% FBS, and minced to yield test food homogenates. The food homogenates were decanted, and 20 μl of each solution containing the different test food particles was added to the cell suspensions in the culture plate. For liquid foods (e.g., breast or cow milk), 2 μl is added instead of the 20 μl diluted food homogenate. An untreated cell suspension was used as a negative control and a cell suspension treated with 2 μg/ml LPS was used a positive control. The 24-well plates containing the cell suspensions and test food treatments were incubated at 37° C. and 5% $CO_2$ for 3 hours. The cells were collected and lysed using QIAshredder and RNEasy Microkit (Qiagen). Reverse transcription and qPCR was performed for gene panels. The results of a 29 gene panel for a single subject are depicted as a color heatmap (FIG. 1), with each food (Y column) against each gene in the panel (X column). A 9-gene panel was measured against a variety of foods, and the heatmap results for two patients tested are depicted in FIG. 2. The values of all genes in the gene panel were added for each food to provide a score. The foods were the arranged, in order from left to right, from lowest to highest score. Foods were identified as safe when the score for the panel is below a threshold level.

False positives, foods that were identified as triggers in the screening, but are actually safe foods for the individual tested, are indicated with a red X. A green checkmark indicates a correct prediction of a safe food. No false negatives (foods that were identified as safe in the screening but are actually trigger foods for the individual tested) were identified for either individual. These experiments demonstrate the power of the test in accurately identifying safe foods for the individual.

Figure 3:
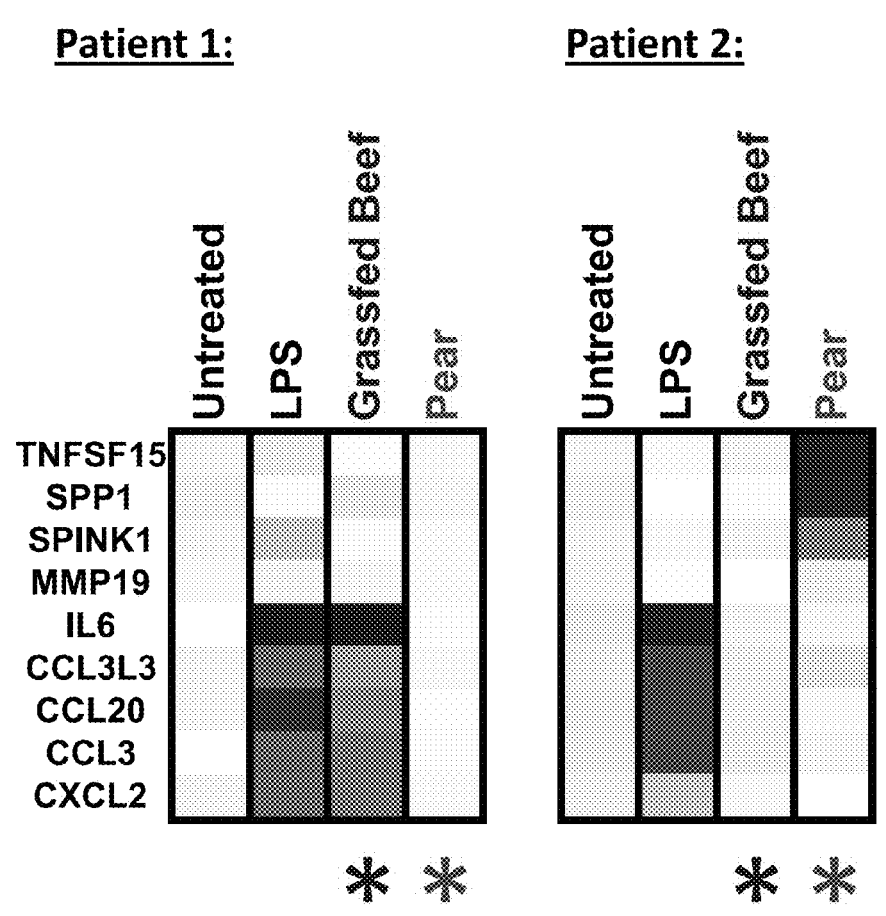
FIG. 3. Comparison of 9-gene transcriptional heatmaps of selected food items for two subjects, demonstrating the individuality of safe/trigger foods.

FIG. 3 demonstrates that the pattern of safe and trigger foods is specific to the individual tested.

REFERENCES

The following references are herein incorporated by reference in their entireties.

1. Nowak-Wegrzyn, A., Chehade, M., Groetch, M. E., Spergel, J. M., Wood, R. A., Allen, K., Atkins, D., Bahna, S., Barad, A. V., Berin, C., et al. 2017. International consensus guidelines for the diagnosis and management of food protein-induced enterocolitis syndrome: Executive summary—Workgroup Report of the Adverse Reactions to Foods Committee, American Academy of Allergy, Asthma & Immunology. J Allergy Clin Immunol 139: 1111-1126 e1114.

2. Nowak-Wegrzyn, A., Jarocka-Cyrta, E., and Moschione Castro, A. 2017. Food Protein-Induced Enterocolitis Syndrome. J Investig Allergol Clin Immunol 27:1-18.

3. Goswami, R., Blazquez, A. B., Kosoy, R., Rahman, A., Nowak-Wegrzyn, A., and Berin, M. C. 2017. Systemic innate immune activation in food protein-induced enterocolitis syndrome. J Allergy Clin Immunol 139:1885-1896 e1889.

4. Jarvinen, K. M., and Nowak-Wegrzyn, A. 2013. Food protein-induced enterocolitis syndrome (FPIES): current management strategies and review of the literature. J Allergy Clin Immunol Pract 1:317-322.

5. Yang, M., Geng, L., Xu, Z., Chen, P., Friesen, C. A., Gong, S., and Li, D. Y. 2015. Severe Food Protein-Induced Enterocolitis Syndrome to Cow's Milk in Infants. Nutrients 8.

6. Hwang, J. B. 2014. Is This Symptom Even a Food Allergy?: Clinical Types of Food Protein-induced Enterocolitis Syndrome. Pediatr Gastroenterol Hepatol Nutr 17:74-79.

7. Kimura, M., Ito, Y., Shimomura, M., Morishita, H., Meguro, T., Adachi, Y., and Seto, S. 2017. Cytokine profile after oral food challenge in infants with food protein-induced enterocolitis syndrome. Allergol Int 66:452-457.

8. Burks, A. W., Casteel, H. B., Fiedorek, S. C., Williams, L. W., and Pumphrey, C. L. 1994. Prospective oral food challenge study of two soybean protein isolates in patients with possible milk or soy protein enterocolitis. Pediatr Allergy Immunol 5:40-45.

9. Hwang, J. B., Sohn, S. M., and Kim, A. S. 2009. Prospective follow-up oral food challenge in food protein-induced enterocolitis syndrome. Arch Dis Child 94:425-428.

10. Nomura, I., Morita, H., Hosokawa, S., Hoshina, H., Fukuie, T., Watanabe, M., Ohtsuka, Y., Shoda, T., Terada, A., Takamasu, T., et al. 2011. Four distinct subtypes of non-IgE-mediated gastrointestinal food allergies in neonates and infants, distinguished by their initial symptoms. J Allergy Clin Immunol 127:685-688 e681-688.

11. Sopo, S. M., Giorgio, V., Dello Iacono, I., Novembre, E., Mori, F., and Onesimo, R. 2012. A multicentre retrospective study of 66 Italian children with food protein-induced enterocolitis syndrome: different management for different phenotypes. Clin Exp Allergy 42:1257-1265.

12. Ruffner, M. A., Ruymann, K., Barni, S., Cianferoni, A., Brown-Whitehorn, T., and Spergel, J. M. 2013. Food protein-induced enterocolitis syndrome: insights from review of a large referral population. J Allergy Clin Immunol Pract 1:343-349.

13. Chung, H. L., Hwang, J. B., Park, J. J., and Kim, S. G. 2002. Expression of transforming growth factor betal, transforming growth factor type I and II receptors, and TNF-alpha in the mucosa of the small intestine in infants with food protein-induced enterocolitis syndrome. J Allergy Clin Immunol 109:150-154.

14. McDonald, P. J., Powell, G. K., and Goldblum, R. M. 1982. Serum D-xylose absorption tests: reproducibility and diagnostic usefulness in food-induced enterocolitis. J Pediatr Gastroenterol Nutr 1:533-536.

15. Berin, M. C. 2015. Immunopathophysiology of food protein-induced enterocolitis syndrome. J Allergy Clin Immunol 135:1108-1113.

16. Katz, Y., and Goldberg, M. R. 2014. Natural history of food protein-induced enterocolitis syndrome. Curr Opin Allergy Clin Immunol 14:229-239.

17. Spergel, J. M. 2006. Nonimmunoglobulin e-mediated immune reactions to foods. Allergy Asthma Clin Immunol 2:78-85.

18. Pena, L. E., Guffey, D., Minard, C. G., Anvari, S., and Davis, C. M. 2017. The role of intravenous access during oral food challenges in food protein-induced enterocolitis syndrome. Allergy Asthma Proc 38:467-473.

19. Yu, L. C. 2012. Intestinal epithelial barrier dysfunction in food hypersensitivity. J Allergy (Cairo) 2012: 596081.

20. Price, D., Ackland, L., and Suphioglu, C. 2013. Nuts 'n' guts: transport of food allergens across the intestinal epithelium. Asia Pac Allergy 3:257-265.

21. Sampson, H. A. 2004. Update on food allergy. J Allergy Clin Immunol 113:805-819; quiz 820.

22. Samadi, N., Klems, M., and Untersmayr, E. 2018. The role of gastrointestinal permeability in food allergy. Ann Allergy Asthma Immunol 121:168-173.

23. Perrier, C., and Corthesy, B. 2011. Gut permeability and food allergies. Clin Exp Allergy 41:20-28.

24. Jarvinen, K. M., Konstantinou, G. N., Pilapil, M., Arrieta, M. C., Noone, S., Sampson, H. A., Meddings, J., and Nowak-Wegrzyn, A. 2013. Intestinal permeability in children with food allergy on specific elimination diets. Pediatr Allergy Immunol 24:589-595.

25. Holbrook, T., Keet, C. A., Frischmeyer-Guerrerio, P. A., and Wood, R. A. 2013. Use of ondansetron for food protein-induced enterocolitis syndrome. J Allergy Clin Immunol 132:1219-1220.

26. Miceli Sopo, S., Battista, A., Greco, M., and Monaco, S. 2014. Ondansetron for food protein-induced enterocolitis syndrome. Int Arch Allergy Immunol 164:137-139.

27. Miceli Sopo, S., Bersani, G., Monaco, S., Cerchiara, G., Lee, E., Campbell, D., and Mehr, S. 2017. Ondansetron in acute food protein-induced enterocolitis syndrome, a retrospective case-control study. Allergy 72:545-551.

28. Bellono, N. W., Bayrer, J. R., Leitch, D. B., Castro, J., Zhang, C., O'Donnell, T. A., Brierley, S. M., Ingraham, H. A., and Julius, D. 2017. Enterochromaffin Cells Are Gut Chemosensors that Couple to Sensory Neural Pathways. Cell 170:185-198 e116.

29. Kidd, M., Gustafsson, B. I., Drozdov, I., and Modlin, I. M. 2009. IL1beta- and LPS-induced serotonin secretion is increased in EC cells derived from Crohn's disease. Neurogastroenterol Motil 21:439-450.

30. Motomura, Y., Ghia, J. E., Wang, H., Akiho, H., El-Sharkawy, R. T., Collins, M., Wan, Y., McLaughlin, J. T., and Khan, W. I. 2008. Enterochromaffin cell and 5-hydroxytryptamine responses to the same infectious agent differ in Th1 and Th2 dominant environments. Gut 57:475-481.

31. Nowak-Wegrzyn, A., and Spergel, J. M. 2017. Food protein-induced enterocolitis syndrome: Not so rare after all! J Allergy Clin Immunol 140:1275-1276.

32. Obuchowski, N. A. 1997. Nonparametric analysis of clustered ROC curve data. Biometrics 53:567-578.

33. Rodriguez, G., and Elo, I. 2003. Intra-class correlation in random-effects models for binary data. The Stata Journal 3:32-46.

The invention claimed is:

1. A method comprising:
(a) growing cells from a subject that suffers from a non-IgE mediated allergic sensitivity in growth media in contact with a food item;
(b) detecting the expression level of a panel of 1000 or fewer biomarkers in the cells, the panel of biomarkers comprising TNFSF15, SPP1, MMP19, IL6,-CCL20, CCL3, CXCL2, CCL3L3, and SPINK1;
(c) comparing the expression level of the biomarkers to threshold and/or control levels of expression for the biomarkers;
(d) determining that the food item is a safe substance because the expression level of the biomarkers is beneath the threshold and/or control levels of expression; and
(e) administering the food item to the subject.

2. The method of claim 1, wherein a food item that is not a safe substance will cause non-IgE mediated allergies in the subject.

3. The method of claim 1, wherein the subject suffers from food protein-induced enterocolitis syndrome (FPIES).

4. The method of claim 1, wherein the subject suffers from eosinophilic esophagitis (EoE).

5. The method of claim 1, further comprising a step of liquifying or homogenizing the food item before adding the food item to the growth media as a liquid or homogenized sample.

6. The method of claim 1, wherein the expression level comprises the RNA expression level.

7. The method of claim 1, wherein the expression level comprises the protein expression level.

8. The method of claim 1, wherein the panel further comprises one or more biomarkers selected from INHBA, F3, TM4SF19, CSF2, FNIP2, GEM, CSF1, EMP1, ZC3H12C, SERPINB2, OR10D3, CCRL2, PPARG, ATF3, IL2A, SOCS3, and TNF.

9. The method of claim 1, wherein the cells are white blood cells.

10. The method of claim 1, wherein the cells are dissociated esophageal cells from mucosal biopsy.

* * * * *